United States Patent [19]

Schubert

[11] Patent Number: 5,202,428
[45] Date of Patent: Apr. 13, 1993

[54] DNA ENCODING NEUROTROPIC GROWTH FACTOR

[75] Inventor: David Schubert, La Jolla, Calif.

[73] Assignee: The Salk Institute for Biological Studies, San Diego, Calif.

[21] Appl. No.: 590,359

[22] Filed: Sep. 27, 1990

Related U.S. Application Data

[63] Continuation-in-part of Ser. No. 541,276, Jun. 20, 1990, abandoned.

[51] Int. Cl.$^5$ ............... C07H 15/12; C07K 13/00
[52] U.S. Cl. .................. 435/320.1; 435/69.51; 435/240.1; 530/399; 536/23.5; 536/23.1
[58] Field of Search ............ 530/399; 536/27; 435/69.51, 240.1, 320.1

[56] References Cited

PUBLICATIONS

Bowie et al. *Science* 247: 1306–1310 (1990).
Burgess et al. *Ann Review Biochem* 58:575–606(1989).
Bey *Ann Rev Neurosci* 7:149–170 (1984).
Watters et al. *J of Neurochem* 49(3):705–713 (1987).
Wagner *J. of Neuroscience* 6(1):61–67 (1986).
Heymanns et al. *Proc. Natl. Acad Sci.* 84:7758–62(1987).
*Nature,* vol. 249, No. 5454, pp. 224–227 (May 17, 1974) Schubert, et al., "Clonal cell lines from the rat central nervous system".
*Proc. Natl. Acad. Sci. USA,* vol. 76, No. 1, pp. 514–517 (Jan. 1979) Bottenstein, et al., "Growth of a rat neuroblastoma cell line in serum-free supplemental medium".
*Proc. Natl. Acad. Sci. USA,* vol. 84, pp. 7768–7772 (Nov. 1987) Porter, et al. "Release of autocrine growth factor by primary and immortalized Schwann cells".
*Annals of Neurology,* vol. 20, No. 3, pp. 317–322 (Sep. 1986) Brockes, et al., "Glial Growth Factor-Like Activity in Schwann Cell Tumors".

*Primary Examiner*—Robert J. Hill, Jr.
*Assistant Examiner*—Shelly J. Guest
*Attorney, Agent, or Firm*—Fitch, Even, Tabin & Flannery

[57] ABSTRACT

Proteins isolated from novel clonal cell lines grown in culture are mitogenic for fibroblasts, and glial cells; some promote nerve cell survival and are prospectively useful in treating diseases such as Parkinson's and Alzheimer's which result in cell death in the nervous system, as well as in treating patients prone to epileptic seizures and patients suffering from trauma to the CNS. Certain of these proteins may be useful in nerve regeneration as well as in treating such diseases and injuries. Some are particularly useful in promoting lung development. The proteins can be topically applied in suitable compositions for wound-healing applications, and they can be administered parenterally to promote lung development and to treat patients afflicted with nerve damage and/or nerve disease.

7 Claims, 6 Drawing Sheets

```
-170                    -150                    -130                    -110                     -90
TGCCCTGTCATTTGAGCCGAACCCTAGGCTGGCAGCTCCAGCTCCTGGAGCCCTGGGCTTCCCGGCCTGGGCTTCCCCGGCGGTGCTCGC

-70                     -50                     -30                     -10
CCGTTGCTTCGGGTTCCGCTGTCTTCCGGCCCGGGAGCCGCTGTCGTGTTGCCGCAGAGACCCGACGCCCGGCCCGGGAACCA 10                       30                       50                              22
 M   R   T   P   S   L   S   L   A   L   S   V   L   S   L   L   V   L   G   S   G   H
ATG AGA ACT CCG TCG CTT TCG CTG GCG CTC TCA GTG CTC CTG TCG CTG CTG GTC CTT GGC TCA GGC CAT 70                       90                      110                     130      44
 Y   A   A   G   L   E   L   N   G   T   S   S   G   K   G   E   P   S   S   G   D   H
TAT GCA GCT GGG TTG GAA CTC AAT GGC ACC TCT AGC TCT GGG AAA GGA GAA CCG TCC TCT GGG GAC CAC 150                      170                      190                              66
 S   A   G   G   L   V   V   S   E   V   S   T   I   S   E   M   P   S   G   S   E   L
AGT GCT GGT GGA CTT GTG GTT TCT GAG GTC TCT ACC ATA AGC GAA ATG CCT TCT GGC AGT GAA CTC 210                      230                      250                              88
 S   T   G   D   Y   D   Y   S   E   E   Y   D   N   E   P   Q   I   S   G   Y   I   V
TCC ACA GGG GAC TAT GAC TAC TCG GAG GAG TAT GAT AAC GAA CCA CAA ATA TCC GGC TAT ATT GTG
```

```
 270          290          310          330  110
  D  D  S  V  R  V  E  Q | V  I  K  P  K  E  N  K  T  E  G  E  K  S
 GAC GAC TCA GTC AGA GTT GAA CAG GTG ATT AAG CCT AAG GAA AAC AAG ACA GAA GGA GAA AAG TCT 350          370          390  132
  S  E  K  P  K  R  K  K  K  G  G  K  G  G  R  N  R  K  K
 TCA GAA AAA CCC AAA AGA AAG AAG AAA GGA GGC AAA GGA GGC AGA AAC AGG AAG AAG 410          430          450  154
  K  N  P  C  A  A  K  F  Q  N  F  C  I  H  G  E  C  R  Y  I  E
 AAA AAG AAT CCG TGT GCC GCC AAG TTT CAG AAC TTC TGC ATT CAT GGT GAA TGC AGA TAC ATC GAG 470          490          510  176
  N  L  E  V  V  T  C  H  Q  D  Y  F  G  E  R  C  G  E  K  T
 AAC CTG GAG GTG GTG ACC TGC CAT CAG GAT TAC TTT GGC GAA CGG TGT GGA GAA AAA ACC 530          550          570          590  198
  M  K  T  Q  K  K  D  D  S  D  L  S  K  I  A  L  A  A  I  V  F
 ATG AAG ACT CAG AAG AAG GAT GAC AGC GAC CTA TCC AAG ATC GCG TTA GCA GCC ATA GTC TTT
```

FIG. 6C

```
     V   S   A   V   S   V   A   A   I   G   I   I   T   A   V   L   L   R   K   R   F   F  220
         610                 620              630                640              650
     GTC TCC GCC GTA AGC GTC GCA AGC GTC ATT ACC GCC ATT GGC GTC CTG CTT CGG AAA CGA TTC TTC

R   E   Y   E   E   A   E   E   R   R   L   R   Q   E   N   G   T   A   H   A         241
         670                 680              690                700              710
     AGG GAA TAT GAA GAA GCA GAA GAA AGA AGG CTG CGG CAA GAA AAC GGG ACT GCA CAT GCC

730
         I   A                                                                              243
     ATA GCC TAG CTGATGGCAATTCAGGATAACAGTCGAGTCACTGCCAAGCCACACCCCACACCGGAAGTGACGAATCGGTCCTTCTTTC
                           750                770              790

810                 830              850                870              890
     AGGGAAGGCTCCAGAGTTCAGTTGTCACTTTTTGTGATAGTCTTATTTCTGTACATAAAGAAAATGTGTGAAGATAAATATTTTT 910                 930              950                970
     CACGTTGTAAATAATTATTAATATTTAAGCGTTATTTATTTTATAGCCCTTAAATGCTTTTTAAACAAAGAAAAAAA
```

DNA ENCODING NEUROTROPIC GROWTH FACTOR

This invention was made with Government support under Grant Nos. NS 09658 and EY 06965 awarded by the National Institutes of Health (NIH). The Government has certain rights in the invention.

This application is a continuation-in-part of U.S. patent application Ser. No. 07/541,276, filed Jun. 20, 1990, now abandoned.

This invention relates to proteins having mitogenic activities and methods of treatment using such growth factors. More particularly, it relates to proteins which are mitogenic to fibroblasts and glial cells and may promote nerve cell survival and induce nerve cell differentiation, and to methods for treating nerve cell diseases and for stimulating lung development.

BACKGROUND OF THE INVENTION

Certain diseases such as Parkinson's and Alzheimer's are the result of cell death in the nervous system. Epileptic seizures also result in cell death. Proteins which cause the survival (and division) of cell types may be of use in treating these diseases as well as in promoting nerve regeneration.

A major cause of blindness is the proliferation of blood vessels into the neural retina (angiogenesis) and the death of photoreceptor cells (various diseases). It is possible that angiogenic protein molecules secreted by certain tumor cells derived from the retina are responsible for aberrant growth of blood vessels into the neural retina in diseases such as diabetic retinopathy. In addition, tumor cell lines from the central nervous system have been under investigation for some time, see, for example: Schubert, D. et al., *Nature*, 249. 224–227 (May 1974) and Bottenstein, J. E. et al., *P.N.A.S.*, 76, 1, 514–517 (January 1979), and such lines are believed to secrete proteins that promote cell division and growth.

Consistent with the foregoing, identification of such proteins would be of substantial value. Such identification should lead to the characterization of such proteins by their amino acid sequences and eventually to the production of such proteins in significant quantities for adequate in vitro and in vivo biological testing, likely by using recombinant DNA methods for their production. Characterization permits the design of agonists and antagonists of such proteins, and antagonists can often be of considerable importance.

SUMMARY OF THE INVENTION

Certain proteins have now been isolated from tumor cell cultures which proteins are shown to have advantageous biological effects. In general, these proteins are mitogenic with respect to fibroblasts and glial cells, and one of them may be highly angiogenic and be a potential cause of retinal blindness. Several of the proteins may also prolong the life of nerve cells in culture and may be useful in promoting nerve cell survival in patients afflicted with diseases wherein there is the frequent occurrence of cell death in the nervous system. These same proteins may also induce nerve cell differentiation. In addition, certain proteins are mitogenic with respect to astrocytes and Schwann cells. The proteins are generally considered to be useful in promoting wound-healing. One of the proteins is also considered to be of therapeutic value in stimulating lung development in premature babies and like situations. Thus, there are provided methods of treatment of patients suffering from nerve cell diseases and methods for promoting lung development, particularly in premature infants.

BRIEF DESCRIPTION OF THE DRAWINGS

FIGS. 6A–6C show the DNA sequence encoding the precursor of the JSC1 protein purified from the JSI cell line, as depicted in FIG. 4, together with the deduced amino acid sequence.

Figure 1:
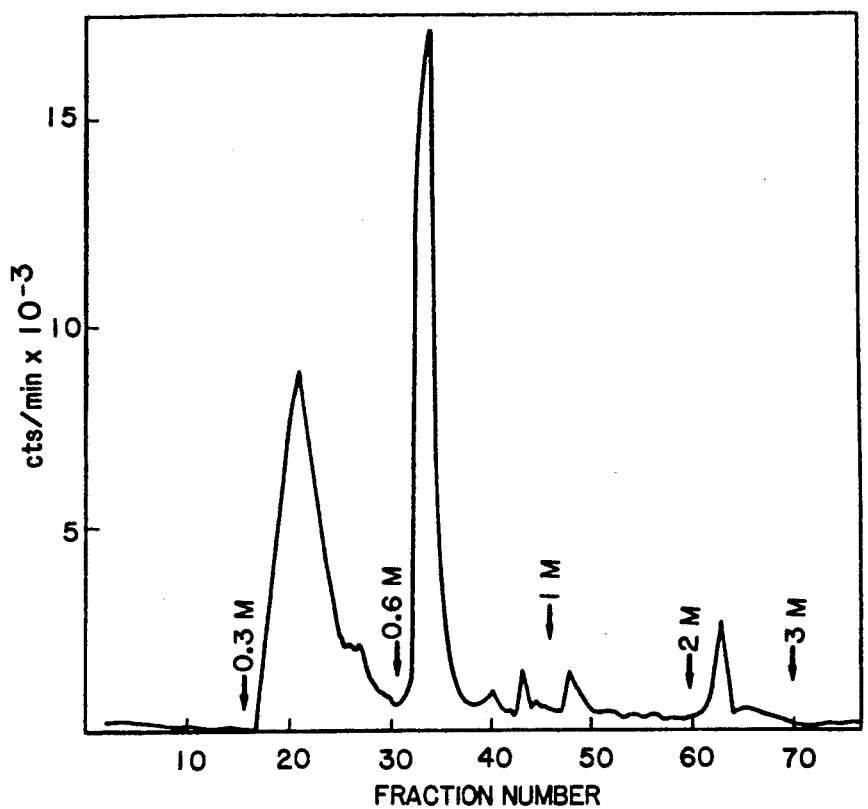
FIG. 1 shows the results of Swiss 3T3 biological assays of the fractions of R33 protein material separated by affinity chromatography using heparin-Sepharose and elution at a 5-step gradient of NaCl concentrations.

The Y-axis in all the FIGURES where the results of biological assays are depicted should be understood to represent counts per minute $\times 10^{-3}$ of tritiated thymidine incorporated into Swiss 3T3 fibroblast cells.

DETAILED DESCRIPTION OF THE PREFERRED EMBODIMENTS

Proteins having mitogenic activities have been isolated from cell cultures of various naturally occurring and artificially induced tumors. The various protein molecules, which are released into the culture media of such tumor cell cultures, are isolated by selection based upon their mitogenic activity using a standard bioassay. The bioassay employed monitors for the ability of the protein to promote the incorporation of tritiated thymidine into Swiss 3T3 cells and is described in detail in the following article: Baird, A. et al., *P.N.A.S.*, 85, 2324–2328 (April 1988). Generally, testing is carried out using a culture of serum-starved 3T3 fibroblast cells which are incubated for 20 hours with the purified protein and then incubated for about 5 hours with radioactive [$^3$H]-thymidine. Substantial incorporation of [$^3$H]-DNA into the cell line is indicative of accelerated cell mitosis.

Following treatment by heparin-Sepharose affinity chromatography and by reverse phase, high performance, liquid chromatography (HPLC-RP) to achieve substantial purification, the purified protein fractions are subjected to electrophoresis on 15% acrylamide gels in 0.1% SDS, which usually results in several bands of protein on the resultant gels. Each band is then individually eluted and assayed for biological activity, again using the Swiss 3T3 cell bioassay. Thereafter, further characterization is carried out of the isolated proteins which show such mitogenic activity to identify the structure of the proteins and to determine other biological properties there of.

Several proteins isolated in the foregoing manner may be useful to promote nerve and glial cell survival, as well as cause the differentiation of embryonic cells to neurons. Moreover, one protein that was isolated and partially purified is angiogenic and may be a potential cause of the proliferation of blood vessels in the neural retina. Antibodies raised against such a protein antigen should be useful in preventing blindness from this particular condition, and once such a protein is completely characterized, the design of useful polypeptide antagonists becomes feasible.

Of the proteins isolated from such tumor cell line cultures, three particular proteins have shown very substantial mitogenic properties for fibroblasts and are expected to be useful in wound-healing, one also stimulates cell division in astrocytes and Schwann cells; another is highly mitogenic to glial cells, e.g. central brain glial cells and peripheral glial cells. The isolation and characterization of each of these proteins is described in detail hereinafter. Although it is possible to obtain these proteins by growing these cell lines and then isolating and purifying the proteins from the culture medium therefrom, it is believed that it will be preferable to produce the proteins synthetically, either by chemical synthesis if the length of the protein chain or subchain is such as to render chemical synthesis commercially feasible or, most preferably, by the use of recombinant DNA methods which are presently well known in this art.

A number of tumor cell lines were adapted to grow in cell culture; these cell lines were each cloned from single cells obtained from tumors that had been induced in newborn rat eyes with nickel subsulfide. Accordingly, each cell line is homogeneous, and each was given a separate number. The cell line designated R33 was found to produce mitogenic proteins which were isolated, purified and identified, as set forth immediately hereinafter.

Serum-free, growth-conditioned medium from the R33 cell line was collected in an amount of approximately 2 liters and was then passed through a 20 ml column of heparin Sepharose (Pharmacia) which had previously been equilibrated with 10 mM Tris-HCl, at pH 7.4 and room temperature. The column was then washed sequentially with 0.01M Tris, pH 7.4 containing the following step gradients of salt: 0.3M, 0.6M, 1M, 2M and 3M NaCl. All of the fractions that were obtained were tested by bioassay. The fractions eluting with the step using the 0.6M salt concentration were found to exhibit very substantial mitogenic activity using the Swiss 3T3 cell assay, the results of which assays for each of the individual fractions are plotted in FIG. 1, and one of the proteins is found to be highly angiogenic.

The 0.6M fraction was then adjusted to a pH of 2, using TFA (trifluoroacetic acid), and pumped onto a Synchropak RP-4 $C_4$ (0.46×25 cm) reverse phase column having a 4000 angstrom particle size and a 300 angstrom pore size. Buffer A is 0.1% (v/v) TFA in water, and Buffer B is 1 ml TFA, 200 ml of water and 799 ml of acetonitrile. 0% Buffer B is used during the initial loading which is carried out at room temperature and a flow rate of about 1 ml/min. Following loading, a straight line gradient is begun in which the amount of Buffer B is gradually uniformly increased from 0 to 80 volume % over 3 hours, as represented partially by the straight line in FIG. 2. Peaks of material exhibiting mitogenic activity elute at about 20% acetonitrile (as depicted by the cross-hatching in FIG. 2), and these peaks are pooled.

The pooled peaks are then subjected to gel electrophoresis. The purified protein material is exposed to 0.1% sodium dodecyl sulfate (SDS) at a pH of 6.8 in a boiling water bath for about 3 minutes and then subsequently applied to a slab gel containing about 15% polyacrylamide (PAGE), as described by Laemmli, U.K., Nature, 227, 680–685 (1970). Protein bands are discovered by silver staining. Several bands are formed, and each is individually electroeluted and then assayed for mitogenic activity. A single band of protein which migrates at about 25 kD (25,000 Subsequent testing of this protein material shows that its activity is lost upon reduction as a result of treatment with about 5% 2-mercaptoethanol at a neutral pH in a boiling water bath for 2 to 3 minutes, allowing the inference that the protein may be a dimer. Subjection of the reduced material to electrophoresis indicates that the dimer appears to consist of two subunits of about 12.5 kD each, which individual subunits do not appear to be mitogenically active. Subjection of the electrophroretically purified protein to microsequencing shows that the N-terminus of the protein is blocked.

Additional tumor cell lines are grown in culture which are each cloned from single cells obtained from a spontaneous tumor that was found in a rat sciatic nerve generating a plurality of homogeneous (clonal) cell lines which appear to be a type indicative of Schwann cell origin. One cell line, arbitrarily marked JS1, was found to release more than one protein exhibiting mitogenic activity; however, the protein of particular interest is hereinafter generally referred to as JSC1.

Figure 3:
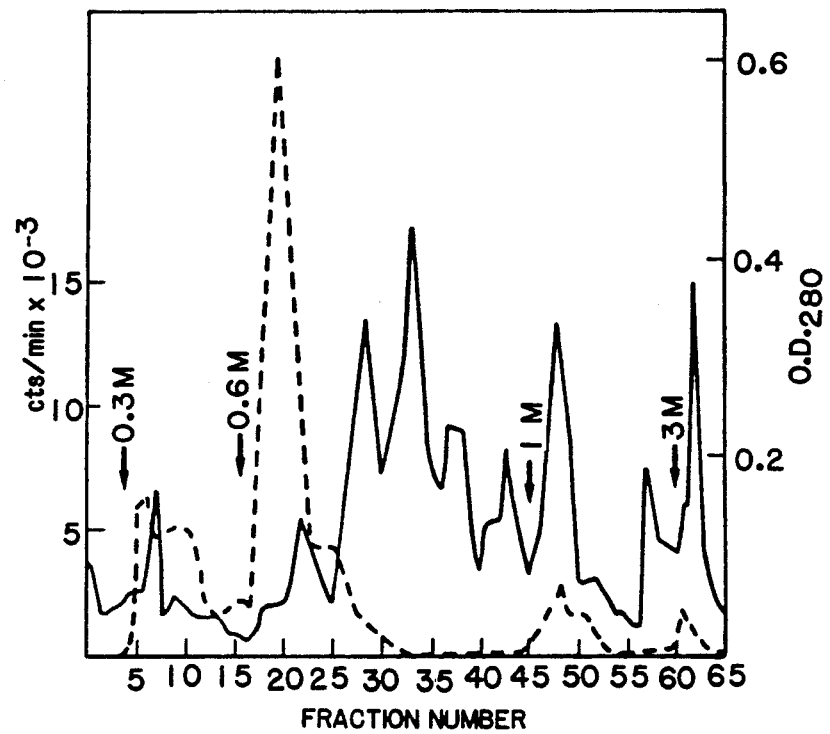
FIGS. 3 and 5 are similar to FIG. 2, showing the results of purifications of protein material from other cell lines labeled JS1 and B-49, with the dashed line of FIG. 3 representing optical density at $280\mu$.
Figure 4:
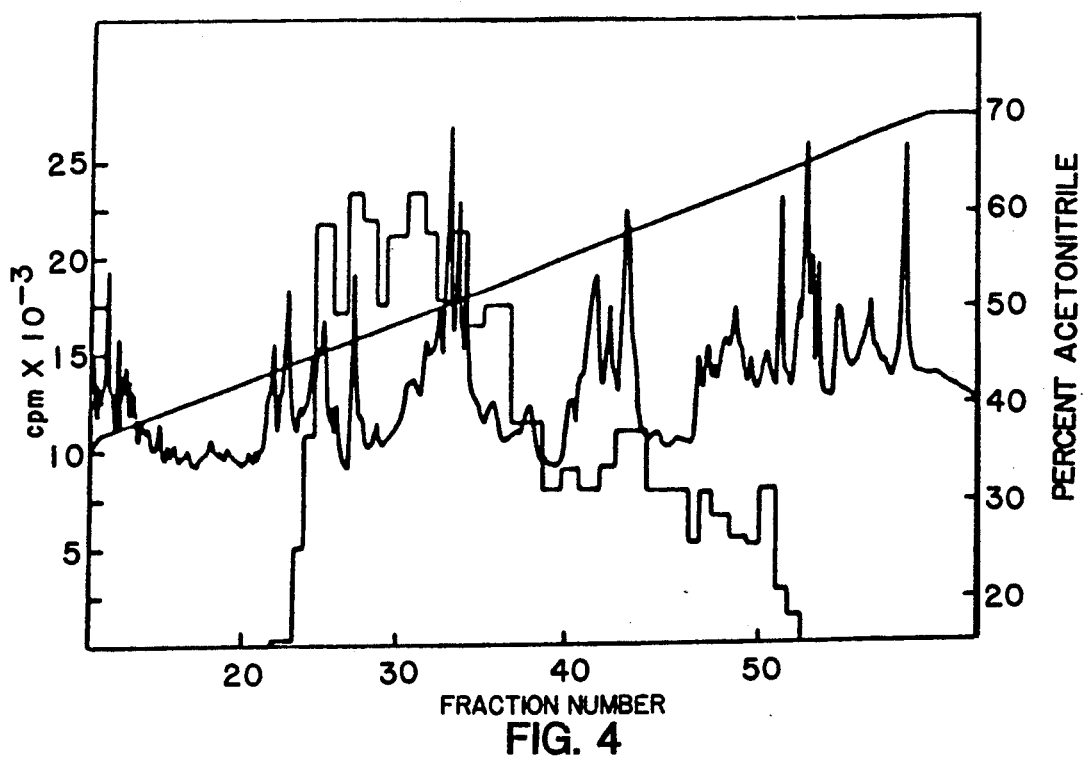
FIG. 4 is similar to FIG. 2, showing the results of HPLC-RP chromatography of the JSC1 protein, following its initial purification as depicted in FIG. 3 with elution using a linear gradient of from 10 to 70 volume percent acetonitrile over 3 hours, with the wavy line representing optical density at 212 nm.

Again, about 2 liters of serum-free, growth-conditioned JS1 cell medium is applied to a 20 ml column of heparin-Sepharose under the conditions described above and then similarly eluted using the same five-step gradient of varying NaCl concentrations. The protein fractions exhibiting mitogenic activity elute near the end of the step with the 0.6M salt concentration, as can be seen by the bioassay plot in FIG. 3. These fractions are then adjusted to a pH of about 2 with TFA, and similarly pumped onto the $C_4$ reverse phase HPLC column described above, under the same conditions described above. Elution from the $C_4$ column is carried out as previously described using a uniform (straight line) gradient of about 10% to 70% acetonitrile B over 3 hours, as shown in FIG. 4. Optical density is continuously monitored at 212 nm. The protein material exhibiting mitogenic activity elutes in several peaks, one of which is at about 48% acetonitrile. Each of these peaks is then electrophoresed as described above.

In some instances, a single band of protein of about 32 kD is detected by the PAGE. This band exhibits mitogenic activity which is lost upon reduction with 2-mercaptoethanol. However, when the reduced material is subjected to electrophoresis, only a single band appears at about 32-35 kD, leading to the inference that the protein may be internally disulfide-linked or otherwise bonded to create a three-dimensional configuration that is lost when exposed to reducing conditions. When the protein material from the HPLC-RP is run on 15% acrylamide gel containing 0.1% SDS and no reducing agent, a major broad band between about 31,000 and 35,000 Daltons is obtained which is cut into equal fractions that are then subjected to microsequencing. Some lower MW bands between about 20 kD and 25 kD are also present. As a result of such microsequencing, it is believed that the N-terminal sequence of the proteins found in various of these fractions is identical, being as follows: Val-Ile-Lys-Pro-Lys-Glu-X-Lys-Thr-Glu-Gly-Glu-Lys-Ser-Ser-Glu-Lys (wherein X may be Asn but is somewhat uncertain). Thus, it is believed that these proteins are fragments of the same molecule, being C-terminally shortened versions of one another, i.e. shortened by the elimination of a peptide sequence beginning at the C-terminus.

The amino acids are referred to herein using the standard 3-letter or 1-letter designations as follows:

| NAME | 3-LETTER | 1-LETTER |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The JSC1 protein is also subjected to assays with astrocyte cell lines, with Schwann cells and with endothial cells. The protein is found to stimulate cell division of both astrocyte and Schwann cells; however, it does not appear to have any effect upon cell division of endothelial cells or of A431 human epidermoid carcinoma cells.

Once a substantial portion of the sequence of mitogen is known, the mRNA encoding the mitogen can be isolated, and the cDNA can be synthesized by recombinant DNA techniques. Messenger RNA (mRNA) is obtained from the JS1 cell line cultures which produce the mitogen, and then cDNA is synthesized from the mRNA by reverse transcription. By inserting such cDNA into cloning vectors, which are then used to transform a suitable host, a cDNA library is created. Suitable probe sets can then be constricted to hybridize with and thereby select clones encoding the protein of interest. cDNA is then excised from the selected clones and inserted into a suitable phage for subcloning for sequence analysis as is well known in this art. Alternatively DNA libraries may be screened by an immunological expression assay with an antibody raised against the mitogen. Such an immunological expression assay may also be used to confirm screening with hybridization probes.

More specifically, based upon the known partial amino acid residue sequence, labelled oligonucleotides are synthesized for use as probes to detect corresponding cDNA. Because of the degeneracy of the genetic code, mixed hybridization probes are prepared and used. Two probe sets, based upon amino acid sequences 1-6 and 8-13, are synthesized and used to select, from such a cDNA library, cDNA clones that contain gene sequences encoding the mitogen of interest. These two probe sets are as follows:

5' GTG—ATC—AAG—CCC—AAG—GA 3'; and
      C     T     A     A     A

-continued

5' AAG—ACC—GAG—GGC—GAG—AA 3'
    A     A     A     G     A

Clones hybridizing with the probes were identified, and one that hybridized with both probe sets was purified.

As a result of sequence analysis of this selected clone, the nucleotide sequence set forth in FIG. 6 is read, from which it is deduced that a protein precursor of 243 amino acids is encoded. It is further concluded that this precursor results in the secretion of a mature protein in the form of a monomer, located 97 AA residues downstream from the initiation of the precursor protein, having either the following sequence of a C-terminally shortened version thereof:

VIKPKENKTEGEKSSEKPKRKKKG

GKGGKGRRNRKKKKNPCAAKFQNFCIHGE-

CRYIENLEVVTCHCHQDYFGERCG

EKTMKTQKKDDSDLSKIALAAIIVFVSAV-

SVAAIGIITAVLLRKRFFREYEEAEERRRLRQENGTAHAIA.

This characterization is in agreement with the earlier analyses of the purified protein material obtained from the JS1 cell line. The indication is that the 19 N-terminal residues may be a signal sequence with the remaining 77 residues likely constituting part of a propeptide originally formed from the 243-residue precursor from which the mature protein is cleaved. The mature protein has a predicted MW of 16,709 Daltons (assuming it includes the full length of 146 residues), and the disparity between the predicted molecular weight for this number of residues and the measured value of about 32K is believed due to glycosylation of the molecule. It is predicted that an N-linked carbohydrate is present at residue 103 in FIG. 6, and it is likely that 0-linked glycosylation occurs at two or more sites in the mature protein.

The purified protein shows half maximal effectiveness in stimulating the cell division of fibroblasts at a concentration of about 15 picomolar. Based upon its similarity to murine EGF (epidermal growth factor), it is predicted that the mature protein contains three disulfide bridges between the cysteine residues in positions 137 and 150, 145 and 161, and 163 and 172, which locations are numbered with respect to the 243-residue precursor shown in FIG. 6. Inasmuch as the JS1 cell line has been identified as a Schwann cell line, the mature protein may be referred to as SDGF, for Schwannoma derived growth factor.

It has been determined that this protein is expressed at high levels in the lungs of newborn mammals. It is considered that the protein will likely have therapeutic value in stimulating lung development in premature babies and in children with incompletely developed lungs, and in this respect, it is thought that the protein stimulates surfactant synthesis. Such surfactants are a mixture of lipoproteins, chiefly lecithin and sphingomyelin, secreted by the great alveolar (type II) cells into the alveoli and respiratory air passages; they reduce the surface tension of pulmonary fluids and thus contribute to the elastic properties of pulmonary tissue.

The peptides would of course be administered under the guidance of a physician and would likely be in the form of a pharmaceutical composition which would contain the peptide in conjunction with a conventional pharmaceutically-acceptable carrier. For treating newborn infants to stimulate lung development, or for the treatment of children with incompletely developed lungs, it is likely that the peptide would be administered intranasally as a part of a saline aerosol containing about 10 μg of the peptide per milliliter; however, it might also be administered intravenously or by another suitable parenteral route, as a part of an appropriate pharmaceutical formulation. Such compositions would contain an appropriate percent of active material by weight, as is common in this art, and the daily dosage would vary with the size and age of the infant or child being treated. For example, a daily dosage of between about 25 micrograms to about 75 micrograms of the peptide, per kilogram of body weight, might be injected into the amniotic fluid in the placenta for treatment of the unborn embryo, with somewhat higher dosages being administered on a daily basis to infants and young children.

Because mitogenic proteins from different mammalian species usually show high homologies, i.e., porcine, human, bovine, ovine and rat, it appears certain that such homologous mitogens from other species can be deduced using the same probes as were employed in searching the rat cDNA libraries. Alternatively, cDNA fragments of the gene sequence coding for the rat mitogen (or the entire sequence) can be used to probe the cDNA library of another species, e.g., human. Thus, the knowledge of the sequence of the rat mitogen allows the present-day molecular biologist to deduce the sequences of the mitogens of other mammalian species (or even nonmammalian species having a homologous protein) and to also prepare such hormones by the use of recombinant DNA technology.

It is believed that the human counterpart of the mature rat protein identified above as the JSC1 protein has been characterized and reported in the literature using the terminology amphiregulin, G. D. Plowman, et al. *Molecular and Cellular Biology*, 10, 5, 1969–1981 (May 1990). In this publication, proteins having either 78 or 84 amino acid residues are reported having the following sequence:

SVRVEQVVKPPQNKTESENTSDKPKRKKKGGKNGKNRRNRKKKNPCNAE

FQNFCIHGECKYIEHLEAVTCKCQQEYFGERCGEK, with the 78-residue protein being the foregoing sequence shortened by 6 residues at the left end or N-terminus. This reported human protein has a homology of about 80 percent with the N-terminal portion of the rat protein JSC1 , with an appropriate adjustment being made for the absence of 1 lysine residue in the portion of human protein corresponding to the sequence of 4 lysine residues that appears at positions 131-134 of the precursor shown in FIG. 6. This human protein in the form of either the 78-residue version or a C-terminally extended version of up to 146 residues is considered to have the same biological potency as the JSC1 protein described above in respect of the biological effects discussed above. The C-terminally extended version of the human homolog could include the following 146 residues:

SVRVEQVVKPPQNKTESENTSDKPKRKKKGGKNGKNRRNRKKKNPCNAEFQNFCIHG-

ECKYIEHLEAVTCKCQQEYFGERCGEKALAAIAAFMSAVILTAVAVITVQLRRQYVR-

KYEGEAEERKKLRQENGNVHAIA or it could be shortened by the elimination of 1 or more residues in sequence starting at the righthand end of the 146-residue sequence.

Tumors that were induced in newborn rats using nitrosoethylurea are used to create another series of cell lines which are grown in culture, each being cloned from a single cell obtained from such tumors, as described in Schubert D. et al., supra. The molecules released into the cell culture from one of the cell lines arbitrarily marked as B-49, which cell line is believed to be of glial origin, were found to exhibit mitogenic activity.

Figure 5:
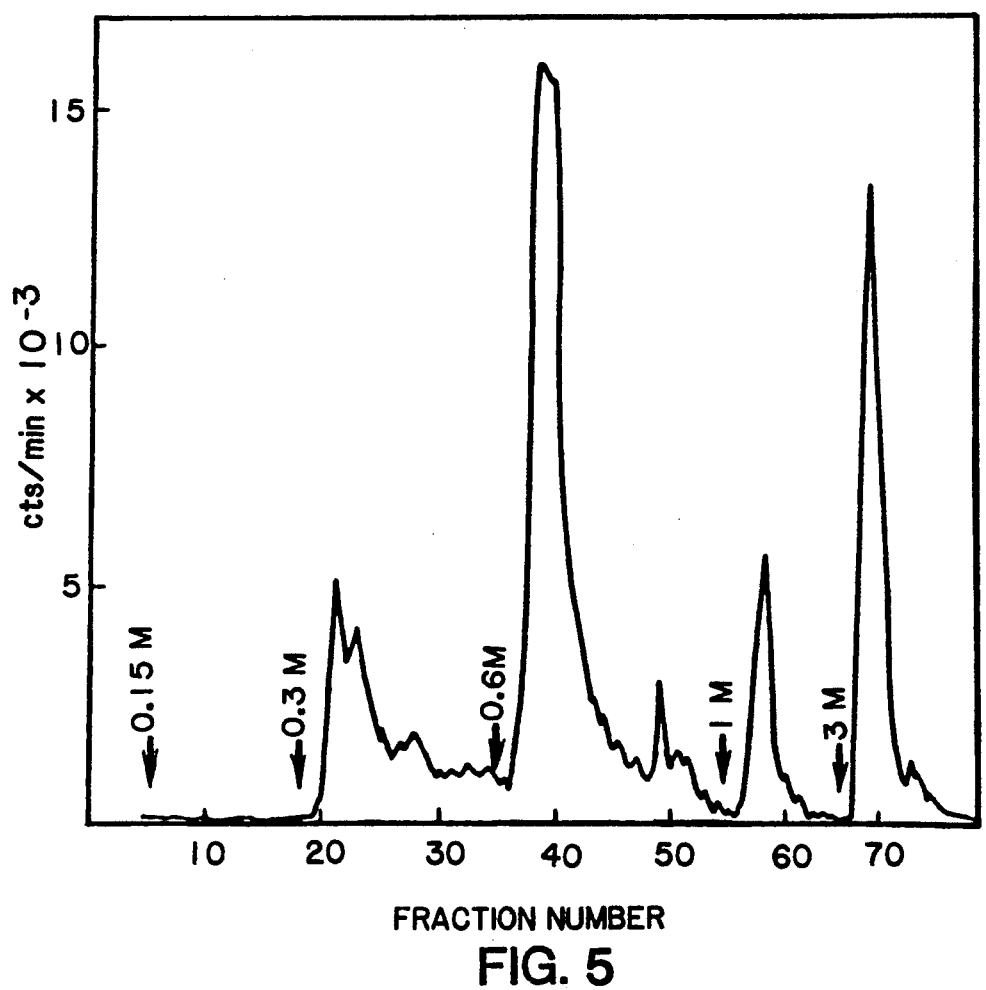

Again, about 2 liters of serum-free, growth-conditioned cell medium from cell line B-49 is applied to a 20 ml column of heparin-Sepharose under the conditions described above and then similarly eluted using a five-step gradient of varying NaCl concentration. Four protein fractions exhibiting mitogenic activity elute at salt gradients of 0.3M, 0.6M, 1.0M and 3.0M, as depicted in FIG. 5. Each of these fractions is then adjusted to a pH of about 2, with TFA, and similarly pumped onto a $C_4$ reverse phase HPLC column as described above, under the same conditions described above. Elution from the $C_4$ column is carried out as previously described using a uniform gradient of about 0 to 70% Buffer B over 3 hours. A single peak exhibiting mitogenic activity elutes at about 30% acetonitrile for each of the four fractions, and each peak is then electrophoresed as described above. Several bands of protein are separated by PAGE for each fraction, and each is individually electroeluted and then assayed for mitogenic activity. A single band which migrates at about 22 kD (22,000 molecular weight) contains all of the proteins which exhibit mitogenic activity. Subsequent testing of this protein material from each of the four fractions shows that its activity is lost upon reduction as a result of treatment with about 5% 2-mercaptoethanol. Subjection of the reduced material to electrophoresis results in a single band at about 11 kD, allowing the inference that protein is a dimer of two identical subunits, which individual subunits do not appear to be mitogenically active.

The purified protein from each of the four fractions is subjected to microsequencing which snows that the N-terminus of each appears to have the following amino acid sequence: Ser-Ile-Glu-Glu-Ala. The longest N-terminal sequence was that obtained from the fraction which eluted at 0.6M NaCl; its sequence was Ser-Ile-Glu-Glu-Ala-Ile-Pro-Ala-Val-X-Lys-Thr-Arg-X-Val-Ile-Tyr-X- wherein X may be Cys. It is believed that all four of the proteins may be portions of the same parent molecule, i.e., C-terminally shortened versions thereof, perhaps shortened versions of the protein PDGF (about 30 kD) or a different form of that molecule. PDGF stands for Platelet Derived Growth Factor and is described in detail in publications of Ross, R. et al, *Cell*, 46, 155-169 (July 1986) and of Nister, M. et al., *P.N.A.S.*, 81, 926-930 (Feb. 1984).

Because these mitogenic proteins are relatively long chain peptides, synthesis by a recombinant DNA technique is the synthetic method of choice, as opposed to standard chain elongation procedures involving stepwise addition of amino acid residues. Although extraction from the media from cell cultures and purification are possible, such is not considered to be a commercially feasible practice at the present time. Accordingly, once an appropriate protein-encoding DNA chain is obtained, e.g., by oligonucleotide synthesis or by probing a cDNA library, as described hereinbefore with respect to the JSC1 mitogen, the synthetic DNA is then inserted into a cloning vector, being appropriately placed therein so as to ensure its expression when the recombinant cloning vector is introduced into an organism or cell line.

As an alternative to construction of a synthetic DNA chain through oligonucleotide synthesis, cDNA corresponding to the protein of interest may be prepared. A cDNA library or an expression library is produced in a conventional manner by reverse transcription from messenger RNA (mRNA) obtained from appropriate mammalian tissue or cell lines. To select clones coding for desired protein sequences, hybridization probes (preferably mixed probes to accommodate the degeneracy of the genetic code) corresponding to likely unique portions of the protein are produced and used to identify clones containing such sequences. Screening of the expression library with antibodies raised against the protein of interest may also be used, alone or in conjunction with hybridization probing, to identify or confirm the presence of the sought-after DNA sequences in DNA library clones. Such techniques are taught, for example in T. Maniatis et al., *Cold Spring Harbor Laboratory Manual*, Cold Spring Harbor, N.Y. (1982), (hereinafter CSH).

A double-stranded DNA chain encoding the protein of interest is constructed or modified with insertion into a particular appropriate cloning vector in mind. Preferably DNA uninterrupted by introns is chosen. The cloning vector that is to be utilized to incorporate the DNA is selected appropriate to its viability and expression in a particular host organism or cell line. The manner of insertion of the DNA depends upon factors particular to the host; for example, if the DNA is to be inserted into a vector for transformation into a prokaryotic cell, such as *E. coli*, the 25 DNA will be inserted 3' of a promoter sequence a Shine-Delgarno sequence (or ribosome binding site) that is within a 5' non-translated portion and an ATG start codon. The ATG start codon is appropriately spaced from the Shine-Delgarno sequence, and the encoding sequence is placed in correct reading frame with the ATG start codon. The cloning vector also provides a 3' non-translated region and a translation termination site. For transfection into a eukaryotic cell, such as a yeast cell or a cell line obtained from a higher animal, e.g., Chinese hamster ovary cells, monkey kidney cells, human liver cells, rat hepatoma cells, TR1 cells and the like, the oligonucleotide sequence encoding the protein of interest is appropriately spaced from a capping site and in correct reading frame with an ATG start signal. The cloning vector should also provide a 3' non-translated region and a translation termination site.

Prokaryotic transformation vectors, such as pBR322, pMB9, Col El, pCRI, RP4 and lambda-phage, are available for insertion of DNA of the length which encodes the protein of interest with substantial assurance of at least some expression of the encoded polypeptide. Typically, such vectors are constructed or modified to have a unique restriction site(s) appropriately positioned relative to a promoter, such as the lac promoter. Other suitable vectors and promoters are disclosed in detail in U.S. Pat. No. 4,798,885, issued Jan. 17, 1989, the disclosure of which is incorporated herein by reference. The DNA chain may be inserted with appropriate linkers into such a restriction site, with substantial assurance of production in a prokaryotic cell line transformed with the recombinant vector. To assure proper reading frame, linkers of various lengths may be provided at the ends of the mitogen-encoding sequences. Alternatively, cassettes, which include sequences, such as the 5' region of the lac Z gene (including the operator, promoter, transcription start site, Shine Delgarno sequence and translation initiation signal), the regulatory region from the tryptophan gene (trp operator, promoter, ribosome binding site and translation initiator), and a fusion gene containing these two promoters called the trp-lac or commonly called the Tac promoter, are available into which the synthetic DNA may be conveniently inserted before the cassette is inserted into a cloning vector of choice.

Similarly, eukaryotic transformation vectors, such as, the cloned bovine papilloma virus genome, the cloned genomes of the murine retroviruses, and eukaryotic cassettes, such as the pSV-2 gpt system (described by Mulligan and Berg, *Nature* 277, 108-114, 1979) the Okayama-Berg cloning system (*Mol. Cell Biol.* 2, 161-170, 1982), and the expression cloning vector described by Genetics Institute (*Science* 228, 810-815, 1985), are available which provide substantial assurance of at least some expression of the protein of interest in the transformed eukaryotic cell line.

For example, the gene segment encoding the JSC1 mitogenic protein, following amplification, might be inserted into the plasmid pYEp, a shuttle vector which can be used to transform both *E. coli* and *Saccharomyces cerevisiae* yeast. Insertion of the synthetic DNA at this point assures that the DNA sequence is under the control of a promoter, in proper reading frame from an ATG signal and properly spaced relative to a cap site. The shuttle vector is used to transform URA3, a strain of *S. cerevisiae* yeast from which the oratate monophosphate decarboxylase gene is deleted.

The transformed yeast is grown in medium to attain log growth. The yeast is separated from its culture medium, and cell lysates are prepared. Pooled cell lysates are determined by RIA to be reactive with antibody raised against the JSC1 protein, demonstrating that a peptide containing such peptide segments is being expressed within the yeast cells. After sufficient growth has been achieved, the mitogenic protein can be recovered from the supernatant using the RP-HPLC purification process described hereinbefore.

An expression vector may also be prepared that places a gene segment obtained from the cDNA shown in FIG. 6 under the control of SV40 promoter (Gorman, C. M., et al, *DNA Protein Engin. Tech.*, 2, 3-10, (1990)) using the expression plasmid pCIS2 and introduced into the 293 human kidney cell line using the calcium phosphate co-precipitation method. The growth-conditioned medium of such transfected 293 human kidney cells revealed mitogenic activity for both Swiss 3T3 cells and primary astrocytes showing that the mature protein of interest is expressed.

As earlier indicated these proteins are mitogenic for a wide variety of normal cultured cells derived from tissue originating from the mesoderm and from the nervous system. These include fibroblast cells, astrocytic glial cells, and cells derived from peripheral nerves, called Schwann cells; the JSC1 mitogen was shown biopotency in stimulating division of all such cells. Thus, these proteins are considered useful for promoting in vitro growth of cultured cell lines, such as cell links that have been transformed by recombinant DNA techniques to produce useful polypeptides; they are also considered to be therapeutically useful in wound-healing, and possibly in the healing of ulcers. The JSC1 protein and mammalian homologs thereof, such as the 78-residue human homolog, are considered to be therapeutically useful to stimulate lung development. Moreover, these proteins have potential therapeutic applications in treating retinal diseases that result in death of nerve cells, CNS injuries where nerve regeneration is required and in treating neural degenerative diseases; they are also prospectively useful in treating diseases such as Parkinson's and Alzheimer's which result in cell death in the nervous system, in treating patients prone to epileptic seizures, as well as in treating various instances where there is trauma to the CNS.

Substantially pure proteins can be routinely obtained having significantly higher purity that proteins that can be extracted from mammalian tissues where they constitute only very minor constituents and are present only in very impure form. Recombinant DNA techniques, for example, can be used to generate organisms or cell lines that produce the target protein in significantly higher proportions relative to total protein, in the cellular material and/or their secretions, as compared to the proportions at which the native protein is present in mammalian tissue. When the starting material from which such synthetic proteins are being isolated has a substantially greater than normal concentration of the target protein, purification techniques can produce more highly purified proteins which are at least about 95% pure (by weight of total proteins) and which is herein referred to as substantially pure. Lower purities may be acceptable when the proteins are used to promote the in vitro growth of cell cultures.

Substantially pure synthetic proteins or the nontoxic salts thereof, combined with a pharmaceutically acceptable carrier to form a pharmaceutical composition, may be parenterally or locally administered to mammals, including humans, for example, intravenously, subcutaneously, intramuscularly, topically or orally, depending upon the particular application intended. Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. Topical applications may utilize the protein together with certain carriers, binders and fillers appropriately selected to create a gel or a lotiol for the treatment of superficial lesions, surgical incisions, burns or the like, as well known in this art.

The required dosage will vary with the particular condition being treated, with the severity of the condition and with the duration of desired treatment. The peptides should be administered under the guidance of a physician, and pharmaceutical compositions will usually contain the peptide in conjunction with a conventional, pharmaceutically-acceptable carrier. For example for wound-healing a standard composition might include the protein at a concentration of about 1-10 weight % with topical application being repeated, e.g. about 5 times per day. As healing progresses, compositions of more dilute form may be used, e.g. about 0.05 to 0.5%. For other applications, concentrations as low as about 1 ng to 1 µg/ml may be used. The proteins may also be used in timed-release systems.

If used to treat patients afflicted with diseases of the nervous system, the peptide JSC1 or its human or other mammalian homolog would preferably be administered parenterally at appropriate daily doses based upon the weight of the patient and the particular affliction. For such treatment, the peptides would also be administered only under the guidance of a physician and as a part of a pharmaceutical composition in combination with a conventional pharmaceutically-acceptable carrier. Such a pharmaceutical composition for intravenous administration might contain an appropriate weight percent of the pepide in saline as is commonly employed in this general field, or it might be administered as a part of a timed-release system. The dosage administered will depend upon the particular affliction being treated, dosages may be employed ranging from about 10 micrograms to about 50 milligrams of the peptide per kilogram of body weight of the patient per day.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. More particularly, it is believed that the JSC1 protein (or its human homolog) can be shortened either at the N-terminus or at the C-terminus, or at both, without losing substantial biological activity for the purposes described hereinbefore, and such C-terminally and/or N-terminally shortened fragments are considered to be equivalents. For example, the JSC1 protein might be shortened to a 79-residue protein in the form of residues 97-175 of FIG. 6. By N-terminally shortened, for example, it is meant that a sequence comprising one or more residues beginning at the N-terminus is deleted from the amino acid sequence of the peptide that is stated herein. Moreover, the JSC1 protein might also be N-terminally extended without detrimental biological effect. By the term "homologous" is meant having a correspondence between amino acid sequences of at least about 60 percent, with adjustments being made for any gap caused by a missing residue(s) in accordance with standard practices for comparison of protein sequences.

Particular features of the invention are emphasized in the claims which follow.

What is claimed is:

1. An essentially purified and isolated recombinant DNA fragment consisting essentially of a DNA sequence encoding a protein including the amino acid sequence:

VIKPKENKTEGEKSSEKPKRKKKG

-continued

GKGGKGRRNRKKKKNPCAAKFQNFCIHGE-

CRYIENLEVVTCHCHQDYFGERCG

EKTMKTQKKDDSDLSKIALAAIIVFVSAV-

SVAAIGIITAVLLRKRFFREYEEAEERRRLRQENGTAHAIA.

2. The DNA fragment of claim 1 which encodes a protein precursor comprising amino acid residues 1–243 of FIG. 6.

3. The DNA fragment of claim 1 wherein there are no interruptions by introns.

4. The DNA fragment of claim 1 having the nucleotide sequence set forth in FIG. 6.

5. A replicable recombinant DNA expression vector which includes the DNA fragment of claim 1, said vector being capable of expressing the DNA in a microorganism or cell culture transformed with said vector.

6. The vector of claim 5 wherein, upon expression, the protein of the amino acid sequence 97–243 of FIG. 6 is produced.

7. Recombinant host cells transformed with the vector of claim 5.

* * * * *

UNITED STATES PATENT AND TRADEMARK OFFICE
CERTIFICATE OF CORRECTION

PATENT NO. : 5,202,428
DATED : April 13, 1993
INVENTOR(S) : Schubert, David

Figure 2:
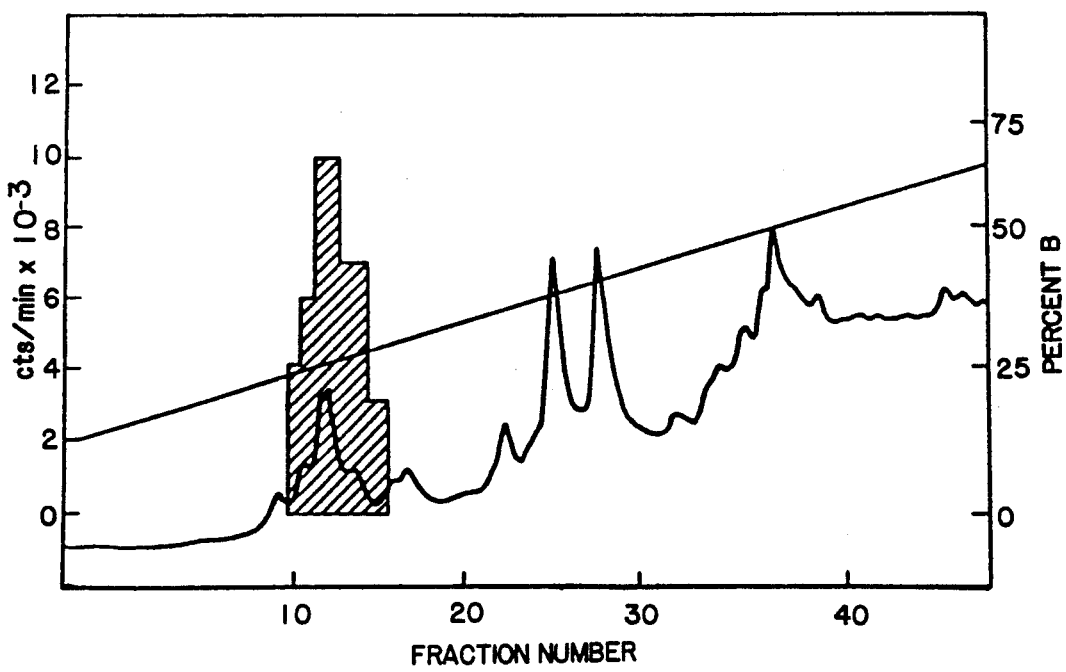
FIG. 2 shows purification of the peak of R33 protein obtained by the FIG. 1 separation, on an HPLC-RP $C_4$ column with elution via a gradient of acetonitrile in 0.1% TFA over 3 hours, measuring optical density at $212\mu$.

It is certified that error appears in the above-indentified patent and that said Letters Patent is hereby corrected as shown below:

Column 2, line 15, change "FIG. 2" to --FIG. 1--. Column 3, line 39, change "heparin Sepharose" to --heparin-Sepharose--. Column 4, line 9, after "(25,000" insert --molecular weight) contains all of the mitogenic activity.-- Column 4, line 67, change "VAl" to --Val--. Column 5, line 45, change "constricted" to --constructed--. Column 6, line 14, change "of" to --or--. Column 8, line 57, change "snows" to --shows--. Column 9, line 51, delete "25". Column 9, line 52, after "sequence" insert a comma (,). Column 10, line 2, change "pcRI" to --pCR1--. Column 11, line 9, change "was" to --has--. Column 11, line 13, change "links" to --lines--. Column 11, line 30, change "that" to --than--. Column 11, line 64, change "lotiol" to --lotion--. Column 12, lines 5-6, after "example" insert a comma (,).

Signed and Sealed this

First Day of March, 1994

BRUCE LEHMAN

Commissioner of Patents and Trademarks